(12) United States Patent
Dineen et al.

(10) Patent No.: US 7,101,472 B2
(45) Date of Patent: Sep. 5, 2006

(54) MICROFLUIDIC ION-SELECTIVE ELECTRODE SENSOR SYSTEM

(75) Inventors: Andrew Dineen, Melrose, MA (US); John R. Williams, Lexington, MA (US); Jennifer Ryan Prince, Stoneham, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 447 days.

(21) Appl. No.: 10/388,202

(22) Filed: Mar. 13, 2003

(65) Prior Publication Data

US 2003/0209451 A1    Nov. 13, 2003

Related U.S. Application Data

(60) Provisional application No. 60/364,213, filed on Mar. 13, 2002.

(51) Int. Cl.
*G01N 27/333* (2006.01)

(52) U.S. Cl. .................. 205/792; 205/789; 204/416; 204/411

(58) Field of Classification Search ........ 204/416–418, 204/409–411, 412; 422/82.03; 205/792, 205/789, 789.5
See application file for complete search history.

(56) References Cited

U.S. PATENT DOCUMENTS

| | | | |
|---|---|---|---|
| 3,923,626 A | 12/1975 | Niedrach et al. | |
| 3,923,627 A | 12/1975 | Niedrach et al. | |
| 3,926,766 A | 12/1975 | Niedrach et al. | |
| 3,957,613 A | 5/1976 | Macur | |
| 4,062,750 A | 12/1977 | Butler | |
| 4,214,968 A | 7/1980 | Battaglia et al. | |
| 4,250,010 A | 2/1981 | Kondo et al. | |
| 4,437,970 A | 3/1984 | Kitajima et al. | |
| 4,517,291 A | 5/1985 | Seago | |
| 4,549,951 A | 10/1985 | Knudson et al. | |
| 4,552,625 A | 11/1985 | Van Der Velden | |
| 4,565,666 A * | 1/1986 | Cahalan et al. | ............. 264/267 |
| 4,654,127 A | 3/1987 | Baker et al. | |
| 4,684,445 A | 8/1987 | Seshimoto et al. | |
| 4,713,165 A | 12/1987 | Conover et al. | |
| 4,772,377 A | 9/1988 | Geist et al. | |
| 4,797,191 A | 1/1989 | Metzner et al. | |
| 4,808,292 A | 2/1989 | Kessler et al. | |
| 4,816,118 A | 3/1989 | Oyama et al. | |
| 4,818,361 A | 4/1989 | Burgess et al. | |
| 4,874,500 A | 10/1989 | Madou et al. | |
| 4,959,130 A | 9/1990 | Josowics et al. | |
| 4,995,402 A | 2/1991 | Smith et al. | |
| 5,004,583 A | 4/1991 | Guruswamy et al. | |
| 5,046,496 A | 9/1991 | Betts et al. | |
| 5,047,044 A | 9/1991 | Smith et al. | |
| 5,112,455 A | 5/1992 | Cozzette et al. | |

(Continued)

FOREIGN PATENT DOCUMENTS

DE    4406908 A1 *   9/1995

(Continued)

OTHER PUBLICATIONS

Derwent abstract of DE 4406908 A1.*

(Continued)

*Primary Examiner*—Alex Noguerola
(74) *Attorney, Agent, or Firm*—Goodwin Procter LLP

(57) ABSTRACT

Ion-selective electrode sensor systems, and methods of fabricating such systems, may be utilized to analyze microfluidic sample volumes, i.e., sample volumes on the order of 1 to 1000 microliters.

25 Claims, 11 Drawing Sheets

U.S. PATENT DOCUMENTS

| | | | |
|---|---|---|---|
| 5,145,565 A * | 9/1992 | Kater et al. | 600/341 |
| 5,183,549 A | 2/1993 | Joseph et al. | |
| 5,186,808 A | 2/1993 | Yamaguchi et al. | |
| 5,194,133 A | 3/1993 | Clark et al. | |
| 5,223,124 A | 6/1993 | Ege | |
| 5,250,168 A | 10/1993 | Tsukada et al. | |
| 5,284,568 A * | 2/1994 | Pace et al. | 204/403.03 |
| 5,312,590 A | 5/1994 | Gunasingham | |
| 5,336,388 A | 8/1994 | Leader et al. | |
| 5,393,401 A | 2/1995 | Knoll | |
| 5,421,981 A | 6/1995 | Leader et al. | |
| 5,425,361 A | 6/1995 | Fenzlein et al. | |
| 5,431,800 A | 7/1995 | Kirchhoff et al. | |
| 5,468,374 A | 11/1995 | Knoll | |
| 5,505,836 A | 4/1996 | Miyahara et al. | |
| 5,545,303 A | 8/1996 | Schasfoort et al. | |
| 5,584,979 A | 12/1996 | Lewenstam et al. | |
| 5,700,360 A | 12/1997 | Chan et al. | |
| 5,804,049 A * | 9/1998 | Chan | 204/418 |
| 5,837,454 A | 11/1998 | Cozzette et al. | |
| 5,840,168 A | 11/1998 | Chaniotakis et al. | |
| 5,865,972 A | 2/1999 | Buffle et al. | |
| 5,911,862 A | 6/1999 | Chan | |
| 5,958,201 A * | 9/1999 | Craig et al. | 204/418 |
| 6,030,827 A | 2/2000 | Davis et al. | |
| 6,060,327 A | 5/2000 | Keen | |
| 6,083,710 A | 7/2000 | Heller et al. | |
| 6,121,009 A | 9/2000 | Heller et al. | |
| 6,123,820 A | 9/2000 | Bergkuist et al. | |
| 6,146,510 A | 11/2000 | Leader et al. | |
| 6,193,864 B1 * | 2/2001 | Leader et al. | 204/403.02 |
| 6,203,758 B1 | 3/2001 | Marks et al. | |
| 6,251,246 B1 | 6/2001 | Chan | |
| 6,284,478 B1 | 9/2001 | Heller et al. | |

FOREIGN PATENT DOCUMENTS

| | | |
|---|---|---|
| JP | 56166461 | 12/1981 |
| JP | 61269056 | 11/1986 |

OTHER PUBLICATIONS

English language translation of Gruenke DE 4406908 A1.*

"Solid-State Ion-Selective Electrode Arrays" by A. Lynch et al., Biomedical Environmental Sensor Technology Center, Dublin City University, Dublin, Ireland, Electroanalysis (1988), 10(16), pp. 1096-1100.

"Solid-state ion sensors with a liquid junction-free polymer membrane-based reference electrode for blood analysis" by H. J. Yoon et al., Sensors and Actuators B 64 (2000), pp. 8-14.

"Introduction to Microengineering" by Danny Banks, http://www.dbanks.demon.co.uk/ueng/chemsens.html, Apr. 26, 1999.

"The Electrochemical Detection of Oxygen, Nitric Oxide and Ascorbic Acid" *The Bio Currents Research Center*, http://www.mbl.edu/labs/BioCurrents/electrochemical/Electrochemical.html.

"A Beginners Guide to Ion-Selective Electrode Measurements" by Chris C. Rundle BSc, PhD., Nico2000 Ltd, London, UK, Version May 5, 2000, http://www.nico2000.net/Book/Guide1.html.

"The RADIOMETER™ Product Line" *by Radiometer Medical A/S*.

"Unmatched speed and simplicity at the Point of Care" *by Radiometer Medical A/S*.

"ABL™ 77 Specifications" *by Radiometer Medical A/S*.

* cited by examiner

MICROFLUIDIC ION-SELECTIVE ELECTRODE SENSOR SYSTEM

CROSS-REFERENCE TO RELATED APPLICATION

This application claims the benefits of and priority to U.S. Provisional Patent Application Serial No. 60/364,213 filed on Mar. 13, 2002, which is owned by the assignee of the instant application and the disclosures of which are incorporated herein by reference in their entirety.

FIELD OF THE INVENTION

The invention relates generally to the field of electrochemical ion sensors, and more particularly to using microfluidic systems with ion-selective electrodes to perform electrolyte measurements.

BACKGROUND OF THE INVENTION

The ionic concentration of a solution can be determined using, for example, spectroscopy, chromatography, calorimetry, optical fluorescence, or a potentiometric titration. These techniques require large laboratory equipment, and are therefore not portable. Indeed, most hospital electrolyte tests are performed in large, multiple-analyte analyzers in a chemistry or medical laboratory. Vials of blood are drawn from the patient for sampling, and hours, and even days, may pass before the caregiver receives the results.

Recently, however, ion-selective electrode technology has made point-of-care (POC) electrolyte testing feasible. For example, the i-STAT system, available from the i-STAT Corporation, utilizes a blood sample that is drawn from the patient and injected into a cartridge including micro-fabricated, ion-selective electrodes, a calibration fluid pouch, and plastic structures for directing fluid flow and storing waste. The fluid pouch, containing known concentrations of the analytes, is punctured at the onset of a test, and the calibration fluid passes over the sensors, allowing a one-point calibration. The fluid is then flushed into the waste container and the blood sample is drawn in for testing. The cartridges are disposable, but are only good for a single use.

While i-STAT's cartridge system represents an improvement to existing POC testing, less-invasive medical diagnostics that incorporate re-usable components, and therefore produce less medical waste and are less-expensive, would be desirable.

SUMMARY OF THE INVENTION

The present invention, in one embodiment, addresses the deficiencies of the prior art by providing an ion-selective electrode sensor system, and methods of fabricating such a system, that may be utilized to analyze microfluidic sample volumes, i.e., sample volumes on the order of 1 to 1000 microliters. For example, the sensor system of the present invention may analyze microfluidic samples of biomedical fluids such as blood, plasma, serum, urine, saliva, and sweat. The system, which only requires a prick of the finger and not a blood draw to acquire a sample, may be used as a miniature POC electrolyte test in hospitals, clinics, physicians' offices, or patients' homes. Moreover, instead of a disposable cartridge with intricate internal structures to perform the calibration process, the system incorporates everything, except the sensor itself, into the analyzing unit. All of the fluid channels, waste disposal, and storage of extra calibration fluid are integrated and therefore reusable, which creates a more cost-effective device.

In one aspect, the invention provides an ion-sensor system including a sampler assembly having a chamber, a connector portion, and an end dimensioned to draw a fluid into the chamber. The ion-sensor system also includes an ion-sensor cartridge including an electrical connection portion interconnecting with the sampler assembly connector portion and a plurality of ion-selective electrodes. In one embodiment, the ion-sensor cartridge includes one or more reference electrodes. The sampler assembly may include an elongated tube having a proximal end and a distal end, where the proximal end is dimensioned to draw a fluid into the chamber by capillary action. In one embodiment, the proximal end has a lancet tip. In various embodiments, the ion-sensor cartridge electrical connection portion is configured as one member of an edge-connector pair or as one member of a pin-and-socket connector pair.

In one embodiment, at least one of the plurality of ion-selective electrodes detects at least one of sodium, chlorine, potassium, and calcium. At least one of the plurality of ion-selective electrodes may have an electrode layer, including silver, and an ion-selective layer, including an ionophore. The ionophore may be valinomycin or N,N,N',N'-tetracyclohexyl-1,2-phenylenedioxydiacetamide. In one embodiment, the ion-sensor system includes an adhesion promoter (e.g., glutyraldehyde) that anchors the ionophore to a substrate or a dielectric layer disposed on a substrate.

In another aspect, the invention provides a method of fabricating an ion-sensor system. The method includes providing a substrate; forming a plurality of ion-selective electrode regions on the substrate; and dividing the substrate into a plurality of strips such that each strip contains a plurality of ion-selective electrodes. The strips are electrically connectable to a sampler assembly. In one embodiment, the method may include forming one or more reference electrode regions on the substrate. Furthermore, the method may include forming an electrical connection portion on the substrate. In one embodiment, at least one of the plurality of ion-selective electrodes detects at least one of sodium, chlorine, potassium, and calcium. At least one of the plurality of ion-selective electrodes may include an electrode layer and an ion-selective layer. In one embodiment, the method includes applying an adhesion promoter (e.g., glutyraldehyde) to the substrate or a dielectric layer disposed on the substrate.

In another aspect, the invention provides an ion-sensor cartridge for use in a sampler assembly. The sampler assembly has a connector portion and an end dimensioned to draw a fluid into a chamber of the sampler assembly. The ion-sensor cartridge includes a plurality of ion-selective electrodes and an electrical connection portion interconnecting with the sampler assembly connector portion.

In a further aspect, the invention provides a method of measuring one or more electrolytes in blood. The method includes extracting blood from a subject, transferring the blood to an ion-sensor cartridge having an ion-selective electrode, and analyzing the electrolyte level of the blood. In one embodiment, the extracting step includes pricking a subject's finger. The transferring step may include drawing the blood into a capillary tube. In one embodiment, the analyzing step includes interfacing the ion-sensor cartridge with an electronic controller.

Other aspects and advantages of the invention will become apparent from the following drawings, detailed description, and claims, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

DESCRIPTION OF THE ILLUSTRATIVE EMBODIMENTS

Ion-selective electrodes include ion-selective layers, or membranes, that will pass only certain species. Ions can be transported across a membrane by a number of processes, including complex formation, diffusion, and drift. Diffusion is driven by a concentration gradient, drift by a potential gradient. Ion transport can also be driven by other sources of energy, for example, thermal conduction or an active ion pump utilizing chemical energy to transport ions across a cell membrane.

In the case of a sodium ion-selective electrode, two compartments, A and B, are separated by a semi-permeable membrane (e.g., permeable to only sodium). If the initial concentration of sodium ions in compartment A is zero, sodium ions will move from compartment B to compartment A since there is a concentration gradient across the membrane. A potential develops that is proportional to the log of the concentration of sodium in each compartment. This potential difference between the two compartments is described by the Nernst equation:

$$\Psi_A - \Psi_B = -\frac{RT}{zF}\ln\frac{[A]}{[B]},$$

where $\Psi_A$ is the electric potential in compartment A, $\Psi_B$ is the electric potential in compartment B, R is the ideal gas constant, T is the temperature in Kelvin, z is the valence charge of the ion being transported, F is Faraday's constant, [A] is the concentration in the first compartment, and [B] is the concentration in the second compartment.

To assign a meaningful value to the electric potential, it is compared to a reference value acquired from a reference electrode. Therefore, while an ion-selective electrode measures the potential in the compartment that contains, ideally, only the ion of interest, a reference electrode measures the potential outside. The reference electrode includes a coating that is electrically conducting, while not favoring the conduction of any particular ion. Examples of suitable electrodes will be described below.

Figure 1:
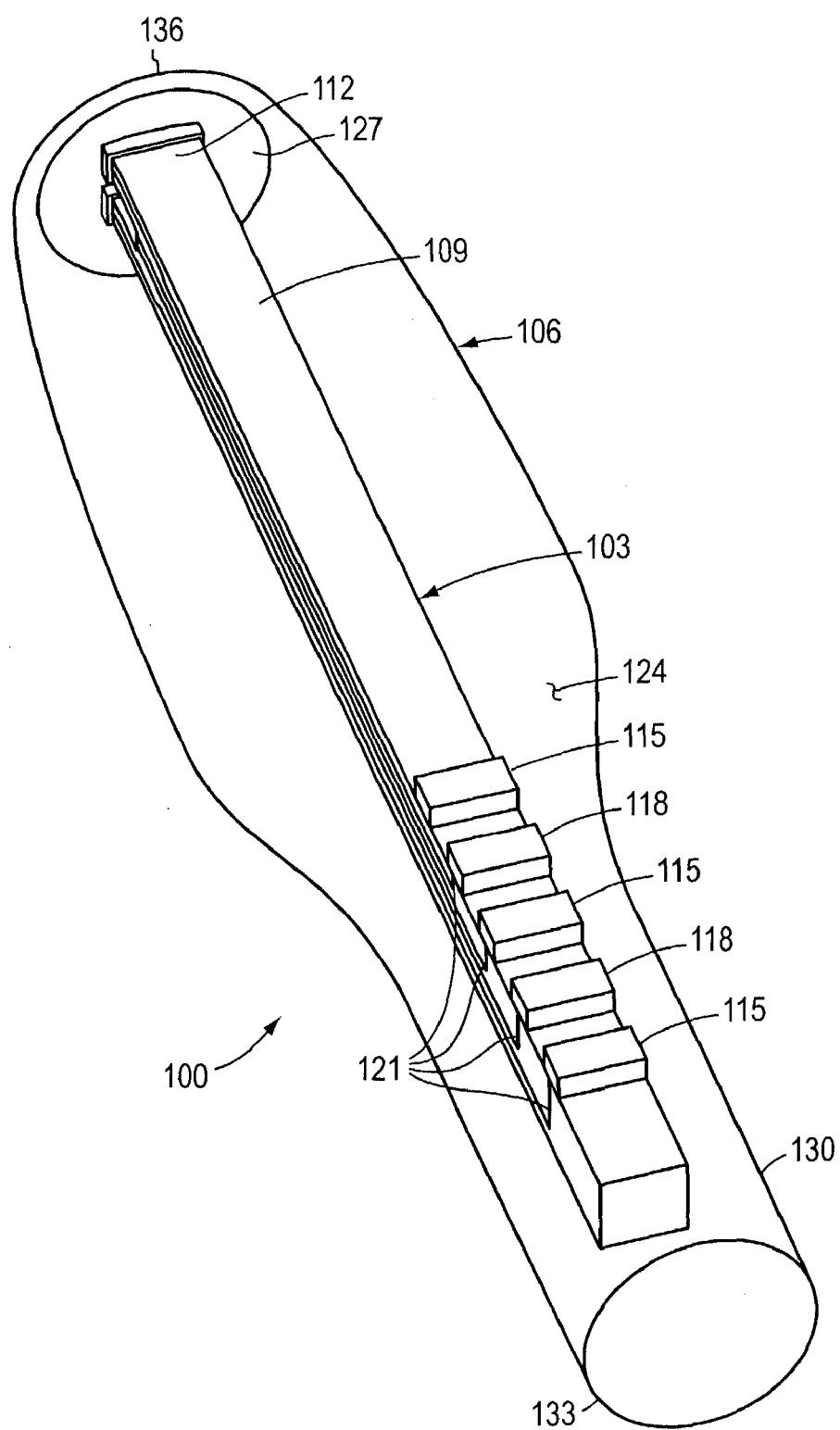
FIG. 1 is a perspective view of an ion-sensor system according to the invention.

FIG. 1 depicts one embodiment of a microfluidic ion-selective electrode sensor system 100 including an ion-sensor cartridge 103 contained in a sampler assembly 106. The ion-sensor cartridge 103 includes an elongated substrate 109 having an electrical connection portion 112 and a plurality of ion-selective electrodes 115. Preferably, the substrate includes one or more reference electrodes 118 and a plurality of lead lines 121 electrically connecting one or more ion-selective electrodes and/or reference electrodes to the electrical connection portion 112. The ion-sensor cartridge 103 is disposed in a chamber 124 of the sampler assembly 106 such that an electrical connection portion 112 at the distal end of the substrate 109 interconnects with a sampler assembly connector portion 127. Preferably, the electrical connection portion of the ion-sensor cartridge and the sampler assembly connector portion are configured such that they may be electrically interconnected by a press-fit as, for example, provided by edge, pin-and-socket, and co-axial connector configurations.

In addition to the connector portion 127, the sampler assembly 106 includes a tubular member 130 having a proximal end 133 and a distal end 136. The proximal end is dimensioned to draw a fluid sample into the chamber 124 by capillary action. In one embodiment, the connector portion 127 is disposed toward the distal end 136 of the tubular member 130.

Accordingly, the invention provides the ability to detect several constituents in a liquid sample. For example, an ion-selective electrode of the invention may be chosen to detect pH (i.e. $H^+$), $Na^+$, $K^+$, $Li^+$, $Ag^+$, $Ca^{2+}$, $Cd^{2+}$, $Ba^{2+}$, $Mg^{2+}$, $Cu^{2+}$, $Pb^{2+}$, $Hg^{2+}$, $Cu^{2+}$, $Fe^{3+}$, ammonium ions ($NH_4^+$), $Cl^-$, $Br^-$, $I^-$, $F^-$, $CN^-$, $OCl^-$, perchlorate ($ClO_4^-$), thiocyanate ($SCN^-$), sulphide ($S^-$), nitrate ($NO_3^-$), nitrite ($NO_2^-$), sulfate ($SO_3^-$), carbonate ($CO_3^-$), bicarbonate ($HCO_3^-$), and/or $S_2O_3^{2-}$. The ion-selective electrodes may be utilized to detect ions by, for example, amperometric, potentiometric, coulombic, condlictometric and/or AC analysis techniques.

Figure 2:
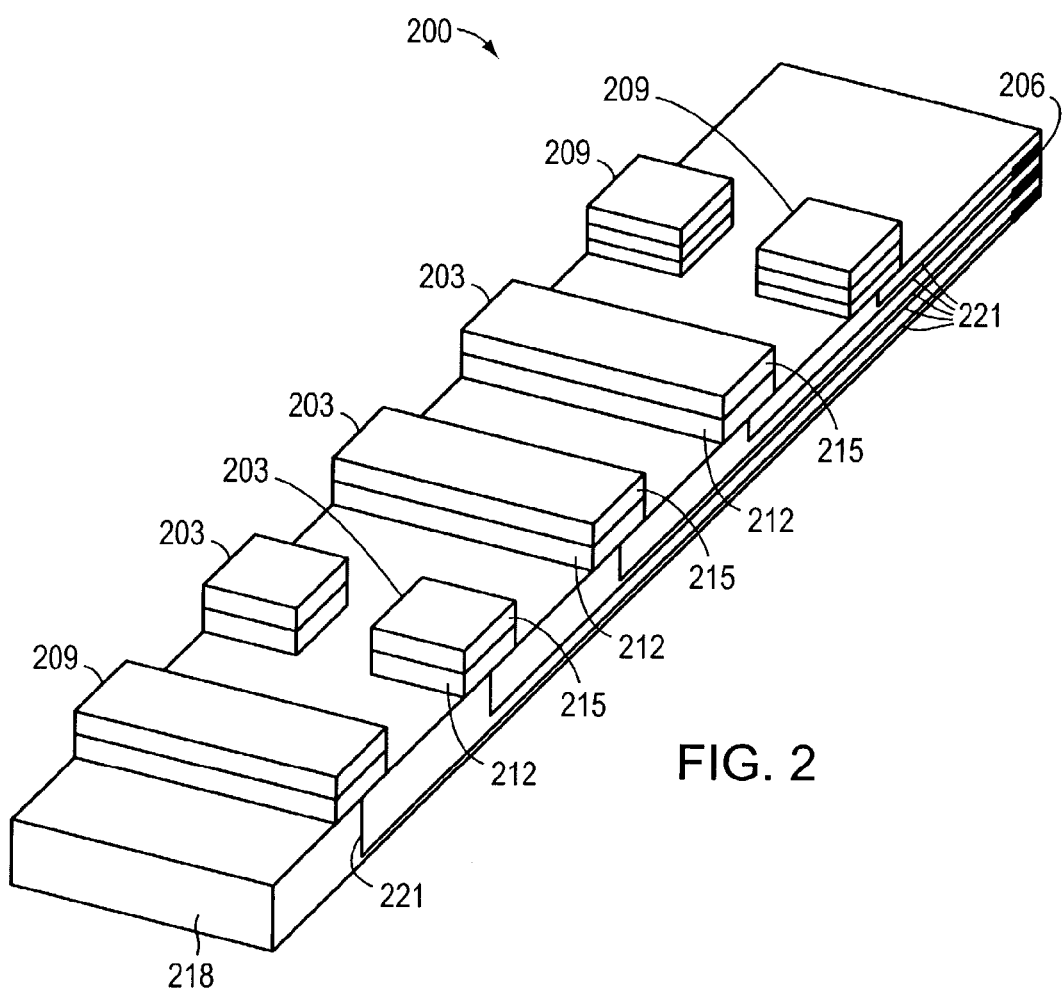
FIG. 2 is a perspective view of an ion-sensor cartridge according to the invention.

FIG. 2 illustrates one embodiment of an ion-sensor cartridge 200. The ion-sensor cartridge includes a plurality of ion-selective electrodes 203, an electrical connection portion 206, and may further include one or more reference electrodes 209. Each ion-selective electrode 203 includes an electrode layer 212 sandwiched between an ion-selective layer 215 and a substrate 218. In one embodiment, the electrode layer includes silver (Ag). Other suitable electrode layers include, but are not limited to, silver/silver chloride (Ag/AgCl), copper (Cu), titanium (Ti), chromium (Cr), gold (Au), platinum (Pt), palladium (Pd), Pd/Ag, platinum black, platinum black/palladium, platinum oxide, iridium (Ir), iridium dioxide ($IrO_2$), and combinations thereof.

In one embodiment, the ion-selective layer includes a doped polymeric material. Suitable polymeric materials include, but are not limited to, polyvinyl chlorides (PVC), polystyrenes, polyacrylates, polycarbonates, polyesters, polyamides, polyurethanes, polyvinylidene chlorides, polyvinyl butyryls, polyvinyl formals, polyvinyl acetates, polyvinyl alcohols, and copolymers of two or more of the above. The dopant may include an ion-selective species such as, for example, a non-dissociable ion-specific, neutral sequestering agent (i.e., an ionophore) or an electrically charged, liquid ion exchanger.

An ionophore is a chemical compound capable of forming a complex with an ion and transporting it through a membrane. The ionophore includes channels that have specific shapes and abilities to bind polar compounds based on the positions of fixed polarities in the molecules in the channel. Ideally, the membrane transports only one ion, but if two ions are similar, a channel designed for one may allow the other also to pass through. The extent to which other ions can diffuse across a membrane is described by the membrane's selectivity coefficient, which can cause deviation from the Nernst equation. The selectivity coefficient is typically measured experimentally, and corrected for by software.

Suitable dopants for a lithium ion-selective electrode include, but are not limited to, N,N'-diheptyl-N,N',5,5'-tetramethyl-3,7-dioxononanediamide, 1,4,7,10-tetraoxyacyclo-decane 12-crown-4, and N,N,N',N'-tetraisobutyl-cis-cyclohexane-1,2-dicarboamide. Suitable dopants for a potassium ion-selective electrode include, but are not limited to, valinomycin, dicyclohexano-18-crown-6, bibenzo-18-crown-6, tetraphenyl borate, and tetrakis p-chlorophenyl borate. Suitable dopants for a calcium ion-selective electrode include, but are not limited to, bis(didecylphosphate), bis(4-octylphenylphosphate), and diethyl N,N'-[(4R,5R)-4,5-dimethyl-1,8-dioxo-3,6-dioxaoctamenthylene]bis(12-methylaminododecanoate). Suitable dopants for a sodium ion-selective electrode include, but are not limited to, nonactin, moenensin, N,N',N"-triheptyl-N,N',N"-trimethyl-4,4',4"-popyllinditris-(3-oxabutyramide), bis[(12-crown-4)methyl] dodecylmethylmalonate, and N,N,N',N'-tetracyclohexyl-1,2-phenylenedioxydiacetamide (ETH 2120). Suitable dopants for a hydrogen ion-selective electrode include, but are not limited to, tridodecylamine, N-octadecyloxy-m-chlorophenylhydrazonemeso-oxalonitrile, and N-octadecyloxy-m-chlorphenylhydrazonemeso-oxalonitrile. Suitable dopants for a chloride ion-selective electrode include, but are not limited to, quaternary ammonium chloride, tributyl tin chloride, and Ag/AgCl.

In another embodiment, the ion-selective layer includes a crystalline material or crystalline membrane. For example, for a fluoride ion-selective electrode, the ion-selective layer may include a lanthanum fluoride crystal that has been doped with europium fluoride, which reduces the resistivity of the crystal.

Preferably, the substrate is fabricated from a semiconductor material such as silicon, silicon carbide, gallium arsenide or combinations thereof. Other suitable substrate materials include, but are not limited to, plastics, refractory oxides, and glasses. As described above, the substrate 218 may include one or more reference electrodes 209. Reference electrodes 209 provide a controlled potential for aqueous and biological fluids over a wide range of ionic strengths and compositions. The substrate may include one reference electrode having both an anion and a cation exchange material. For example, a reference electrode may include a solution of 0.6% tridodecylmethylammonium chloride, 0.5% potassium tetrakis (para-chlorophenyl) borate in an aromatic polyurethane dissolved in dimethylformamide (DMF). The solution is applied as a coating and dried in place. Alternatively, the substrate may include one reference electrode for the cation-selective electrodes and another reference electrode for the anion-selective electrodes. Suitable reference electrodes for cation-selective electrodes include, but are not limited to, Ag/AgCl and Ag/AgCl with, for example, a hydrophilic polyurethane, UV-curable polyurethane, and/or UV-curable epoxy. Suitable reference electrodes for anion-selective electrodes include, but are not limited to, Ag/AgCl.

Preferably, the ion-sensor cartridge also contains lead lines 221 that electrically connect one or more ion-selective electrodes 203 and/or reference electrodes 209 to the electrical connection portion 206 of the ion-sensor cartridge 200. The lead lines may be formed (e.g., by affixation or by deposition by, for example, screen printing) on a surface of the substrate, disposed within the substrate, or both. Suitable lead line materials include any sufficiently conductive material to electrically connect an ion-selective electrode or reference electrode to the electrical connection portion of the ion-sensor cartridge. Examples of suitable lead line materials include, but are not limited to, metals such as Ag, Au, Pt, Cu, Ti, nickel (Ni), and layered combinations and alloys thereof, metal oxides such as indium tin oxide (ITO), and conductive polymers such as poly(pyrrole), poly(N-methylpyrrole), poly(3-methylthiopene) and poly(o-anisidine).

Figure 3:
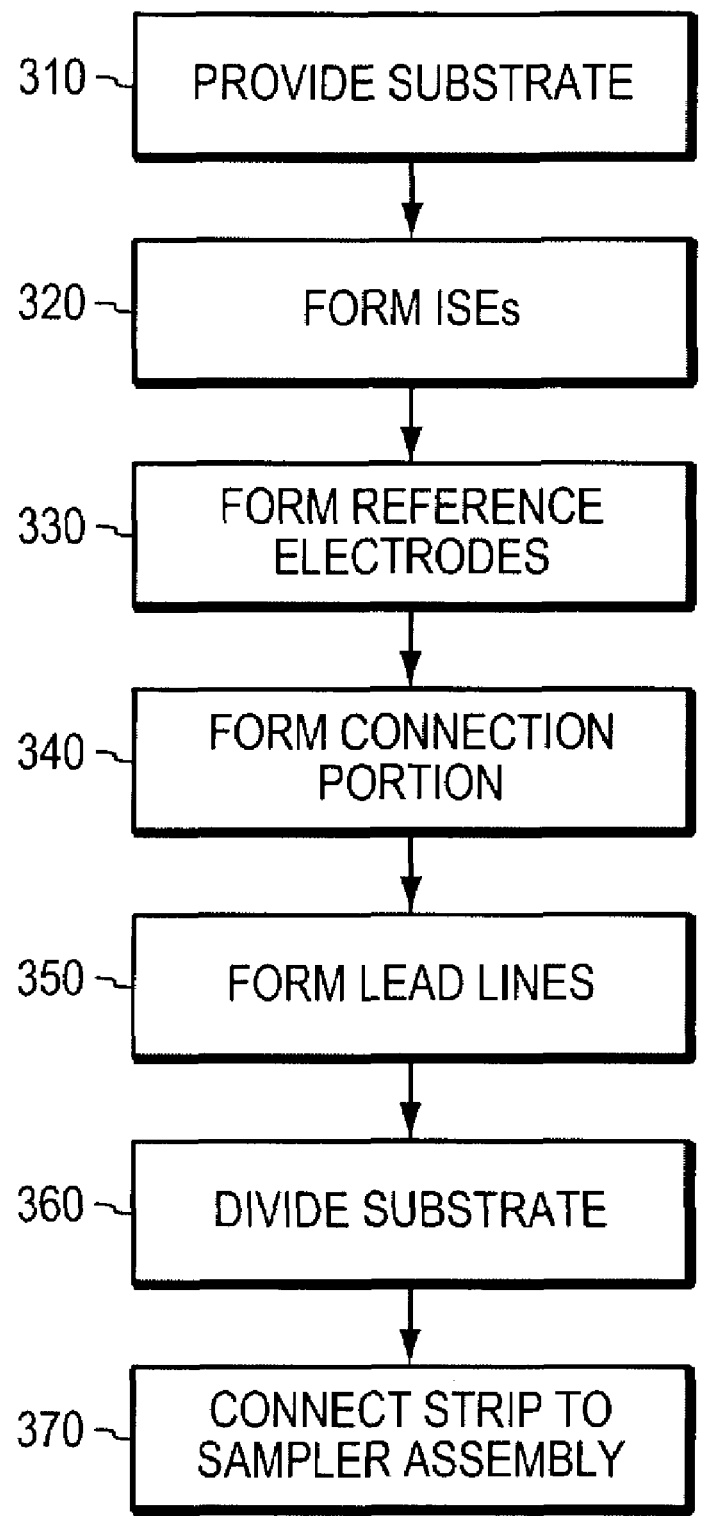
FIG. 3 is a flow diagram that illustrates the steps for fabricating an ion-sensor system according to the invention.

FIG. 3 shows one embodiment of a method for fabricating an ion-sensor system. A substrate is provided (step 310), and a plurality of ion-selective electrodes (ISEs) are formed on the substrate (step 320). Preferably, the substrate is monolithic and includes silicon, silicon nitride, or borosilicate glass, between about 500 μm to about 2000 μm thick. In addition, the substrate is preferably several times as wide as a strip including a plurality of ion-selective electrodes (e.g., an ion-sensor cartridge) will be. In one embodiment, the ion-selective electrodes are formed by first depositing a stripe of electrode material on the substrate to form an electrode layer preferably from about 500 Å to about 5 μm thick. The electrode material may be deposited, for example, by screen printing, vapor deposition, electrodeposition, chemical vapor deposition, sputtering, or any other suitable deposition method. Next, an ion-selective material is deposited on the electrode layer to form an ion-selective layer, preferably from about 1 μm to about 5 μm thick. The electrode material may be deposited, for example, by screen printing, mechanical dispensing, or any other suitable deposition method. In one embodiment, the ion-selective material includes a doped polymeric material. This ion-selective material may be prepared, for example, by dissolving a dopant with the polymeric material in a suitable solvent. Suitable solvents include, but are not limited to, DMF and tetrahydrofuran (THF).

In various embodiments, the polymeric material/dopant solution may include a plasticizer. Suitable plasticizers include, but are not limited to, o-nitrophenyl-octylether, dimethylphthalate, bis(2-ethylhexyl)adipate (DOA), bis(2-ethylhexyl)sebacate (DOS), dioctylphenyl-phosphonate, dibutylphthalate, dioctylphthalate, dibutyladipate, hexamethylphosphoramide, diundecylphthalate, and dioctyl sebacate. The polymeric material/dopant solution may be deposited on the electrode layer by, for example, screen printing, pneumatic dispensation, and/or spin casting. A sufficient fraction of solvent is then removed to form an ion-selective layer.

An adhesion promoter may be applied to the substrate or a dielectric layer disposed on the substrate to enhance the adhesion of the ionophore to the substrate or dielectric layer. The dielectric layer maintains electrical isolation between the conductive paths on the surface of the cartridges. The dielectric material may be a spun-on or a deposited organic dielectric such as a polyimide, a photoimagable dielectric, or an inorganic material such as silicon dioxide.

When the substrate material is either glass or silicon, a solution of ethanol, water, and a siloxane may be used. The siloxane preferably includes a functional group at each of the two ends of a long-chain molecule. One end bonds with an OH-terminated substrate (e.g., silicon or glass) and the other bonds to the ionophore. Suitable siloxanes include hexamethyldisiloxane. If the substrate includes a polyurethane-based polymer, then 3-aminopropyltri-methoxysilane or 3-aminopropyltriethoxysilane is generally used. If the substrate includes a polyimide-based dielectric coating, then glutyraldehyde may serve as the adhesion promoter.

The method of fabrication may include a step of forming one or more reference electrodes on the substrate (step 330). In one embodiment, the method forms one or more cation reference electrodes and one or more anion reference electrodes. The cation and/or anion reference electrode may, for example, consist of or include Ag or Ag/AgCl.

In one embodiment, a Ag/AgCl reference electrode is formed by first depositing an electrode layer on the substrate. Second, if the electrode layer is not silver, then a silver layer is deposited on the electrode layer. Third, a silver chloride layer is formed by, for example, chlorination by oxidation with a ferric chloride ($FeCl_3$) solution, or by electrolysis by means of a KCl solution. Fourth, the Ag/AgCl layer is coated with an ion-exchange material such as, for example, a doped polymeric material or ion exchange resin. In another embodiment, the formation of a Ag/AgCl reference electrode includes deposition of a solid electrolyte layer on the AgCl layer instead of an ion-exchange material, and coating the solid electrolyte layer with an ion-exchange material.

Referring again to FIG. 3, the method of fabrication may include a step of forming an electrical connection portion on the substrate (step 340) and/or a step of forming lead lines that electrically connect one or more of the ion-selective electrodes and/or reference electrodes to an electrical connection portion (step 350). The electrical connection portion and lead lines may include any conductive material suitable for electrically interconnecting the ion-selective electrodes with a sampler assembly. Suitable conductive materials include, but are not limited to, metals such as Ag, Au, Pt, Cu, Ti, Ni, and combinations and alloys thereof, metal oxides such as indium tin oxide (ITO), and conductive polymers such as poly(pyrrole), poly(N-methylpyrrole), poly(3-methylthiopene) and poly(o-anisidine). Other conductive materials such as silver-filled epoxies may be used. Suitable electrical connection portion and lead line formation techniques include, for example, screen printing, lithography, vapor deposition, or electrodeposition.

It should be recognized that the steps of forming ion-selective electrodes, one or more reference electrodes, an electrical connection portion, and lead lines (steps 320 to 350) may be performed in any order. In addition, two or more of these steps may performed substantially concurrently. For example, where a reference electrode includes an electrode layer, the electrode layers of the reference electrode and one or more ion-selective electrodes may be deposited in the same step. Other combinations and concurrent performances of these steps will be readily apparent to one of ordinary skill in the art from the description of the present invention.

With continued reference to FIG. 3, subsequent to ion-selective electrode, reference electrode, electrical connection portion, and/or lead line formation, the substrate is divided into longitudinal strips (step 360) such that at least two or more of the strips include a plurality of ion-selective electrodes (as illustrated, for example, in FIG. 2). A longitudinal strip is then electrically connected to a sampler assembly (step 370) to form an ion-sensor system. In one embodiment, where the strip includes an electrical connection portion and the sampler assembly includes a connector portion, the electrical connection portion and sampler assembly connector portion are electrically interconnected. Preferably, the strip electrical connection portion and the sampler assembly connector portion are configured such that they may be electrically interconnected by a press-fit.

Figure 4A:
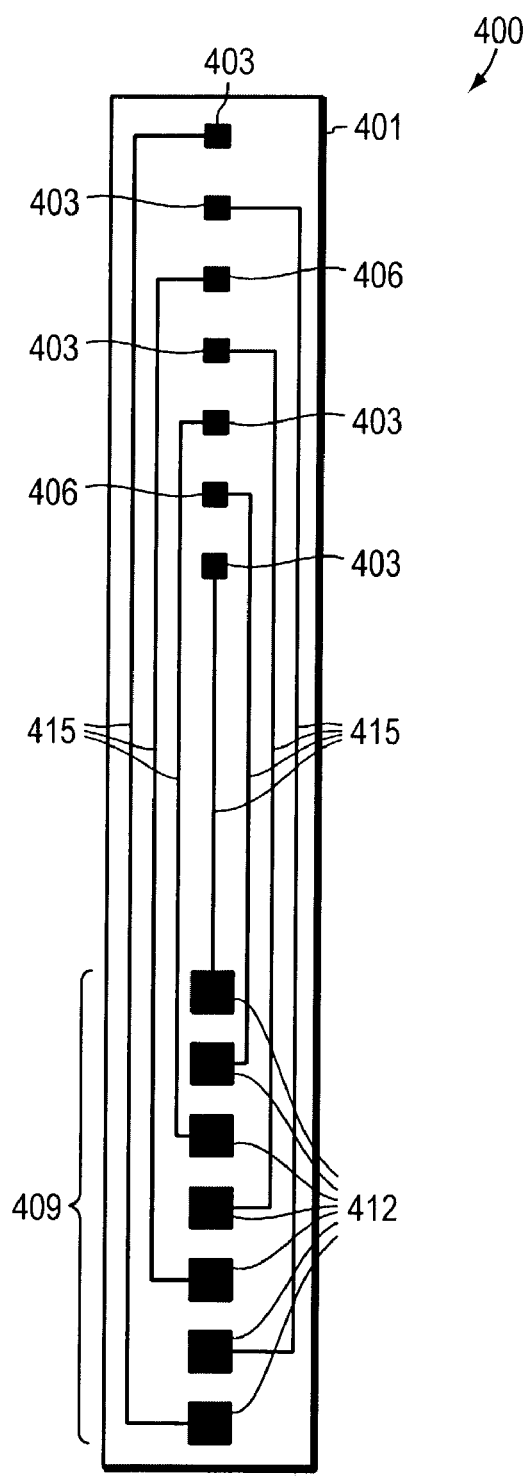
FIG. 4A is a plan view of another embodiment of an ion-sensor cartridge according to the invention.
Figure 4B:
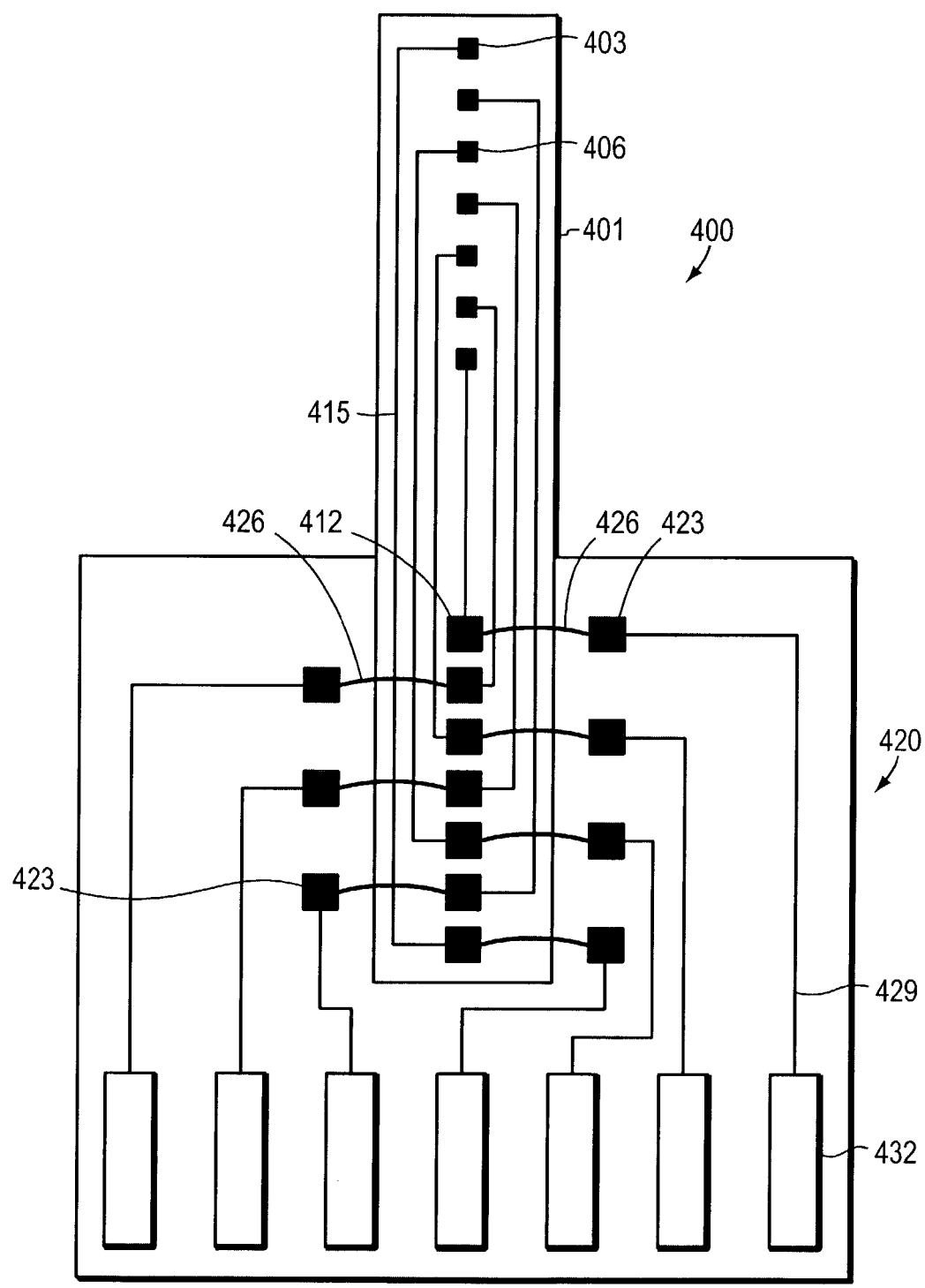
FIG. 4B is a plan view of an embodiment of an ion-sensor cartridge interfaced with a sampler assembly connector portion according to the invention.

FIGS. 4A–4D depict various illustrative embodiments of an ion-sensor system and the components thereof. FIG. 4A illustrates one embodiment of an ion-sensor cartridge 400. The ion-sensor cartridge includes a substrate 401 having a plurality of ion-selective electrodes 403, one or more reference electrodes 406, and an electrical connection portion 409 including of a plurality of contact pads 412. Lead lines 415 electrically connect the ion-selective electrodes 403 and reference electrodes 406 to the contact pads 412. Referring to FIGS. 4A and 4B, the contact pads 412 facilitate interconnection with a sampler assembly connector portion 420. The electrical connection portion 409 and the connector portion 420 are preferably configured such that they may be electrically interconnected by a press-fit.

In one embodiment, the connector portion 420 includes a series of connector pads 423 and connection leads 426. The connection leads 426 electrically connect the contact pads 412 of the ion-sensor cartridge 400 to the connector pads 423 of the connector portion 420. The connection leads 426 may include any suitable electrically conductive material such as, for example, metals and conductive polymers. The connection leads 426 may be electrically connected to the contact pads 412, and/or connector pads 423, by a press-fit. The connection leads 426 may be electrically connected to the contact pads 412, and/or connector pads 423, by gold wire ball bonding, soldering, welding or attachment with a suitable conductive adhesive. The connection leads 426 may take many forms. For example, the connection leads 426 may be in the form of pins, wires, ribbons, tabs, and/or fingers. After these electrical connections have been made, the contact pads 412, connector pads 423, and/or connection leads 426 may be coated with a protective layer of silicone or other hydrophobic material.

Figure 4C:
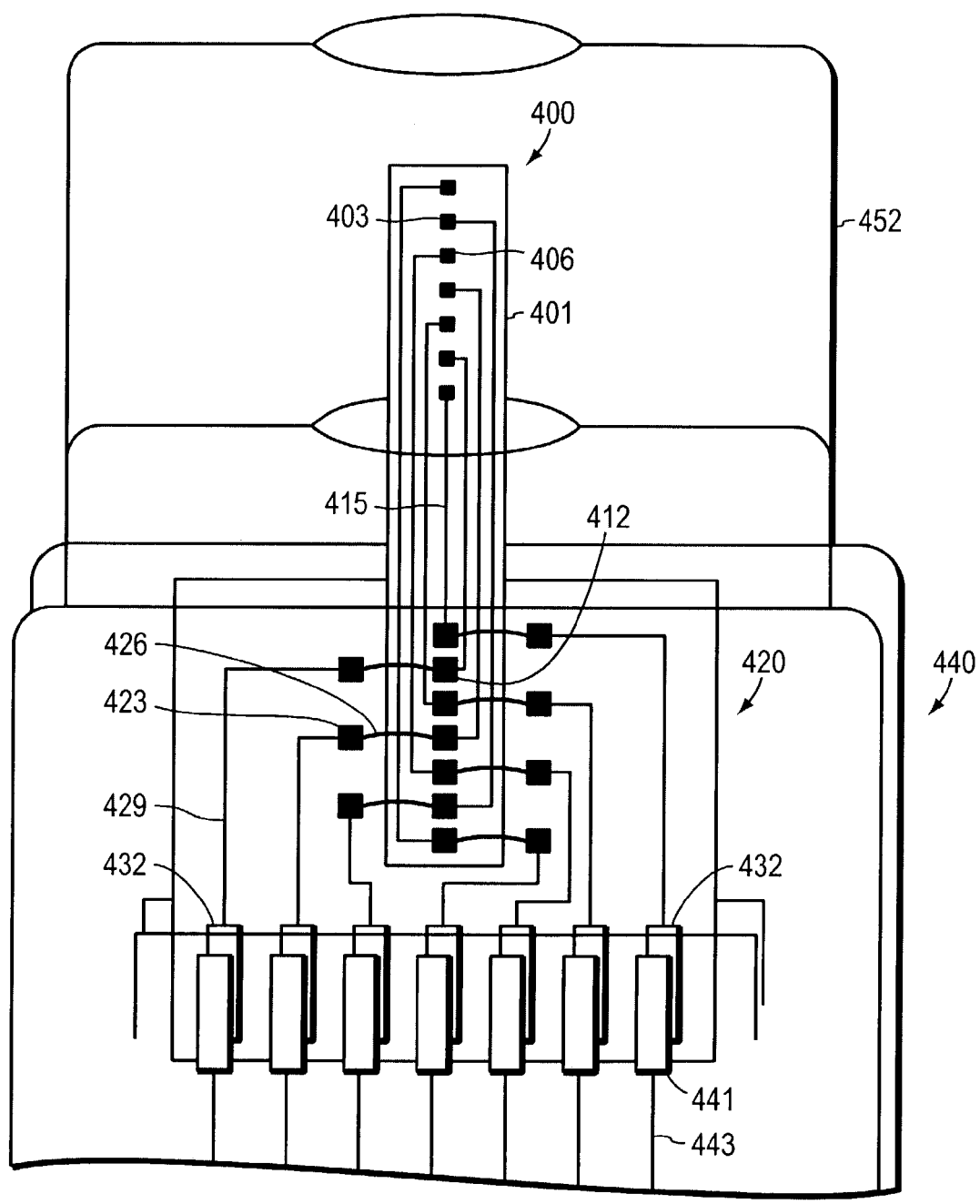
FIG. 4C schematically illustrates an ion-sensor cartridge interfaced with a sampler assembly connector portion and including guide structures according to the invention.

Preferably, the connector portion 420 includes structures that facilitate electrical connection of the ion-sensor system to another electrical device such as a sensor readout. In one embodiment, the connector portion 420 includes interface leads 429 that electrically connect the connector pads 423 to corresponding interface contacts 432. Referring to FIGS. 4B and 4C, the interface contacts 432 in turn facilitate electrical connection of the connector portion 420 to another device or connector 440 (e.g., a cable or device head).

Figure 4D:
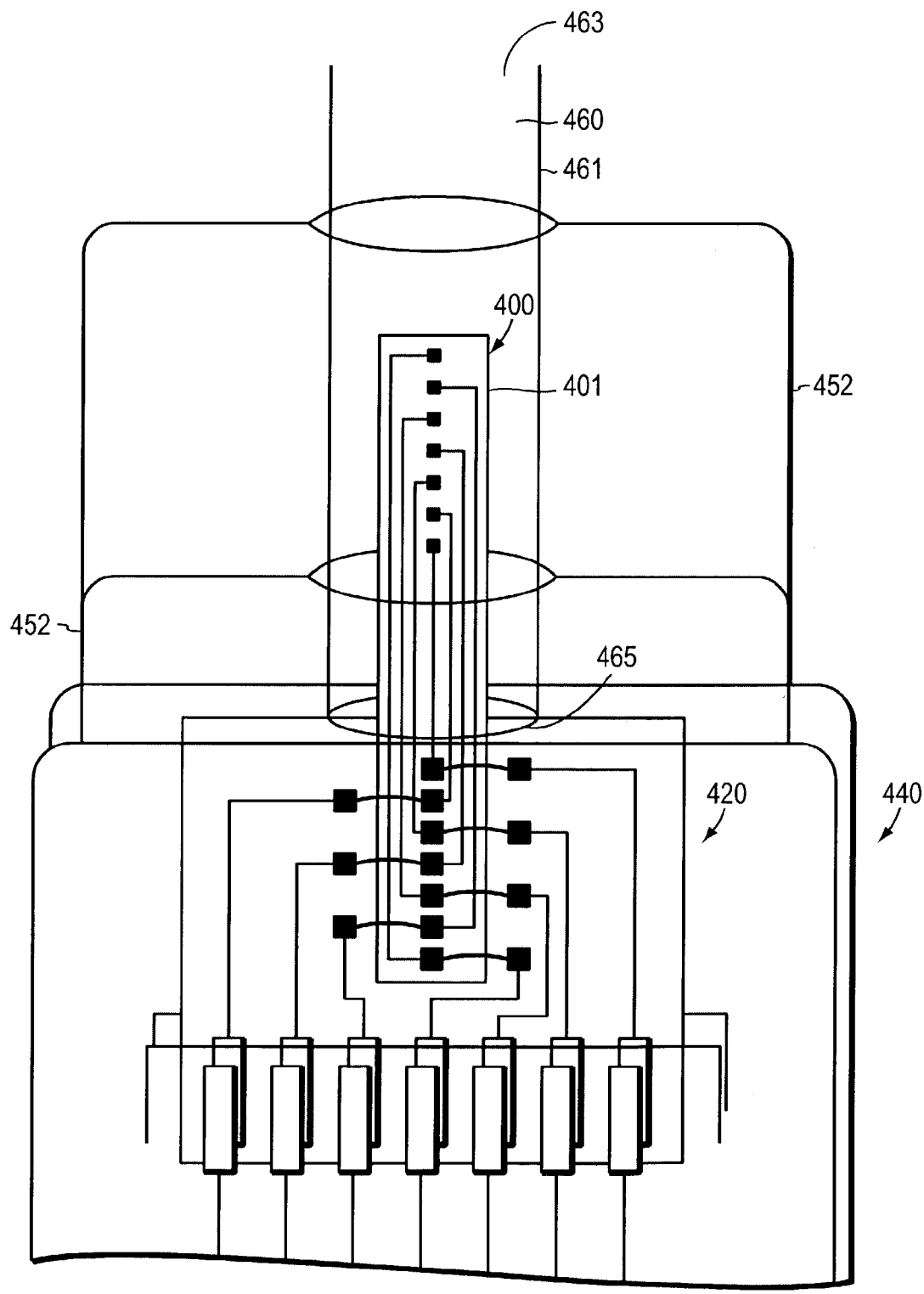
FIG. 4D schematically illustrates an ion-sensor system including a sampler assembly chamber according to the invention.

Referring to FIGS. 4C and 4D, in one embodiment, the interface contacts 432 electrically connect the connector portion 420 to corresponding device contacts 441. The device contacts 441 in turn electrically connect the connector portion 420 to the electrical device (not shown) via the device leads 443. The device contacts 441 may be configured such that they are electrically connected to the interface contacts 432 by a press-fit. Alternatively, the device contacts 441 may be electrically connected to the interface contacts 432 by gold wire ball bonding, soldering, welding, or attachment with a suitable adhesive. After these electrical connections have been made, the interface leads 429, the interface contacts 432 and/or device contacts 441 may be coated with a protective layer of silicone.

The device 440 may also include a holder that facilitates construction and/or testing of the ion-sensor system. For example, the device 440 may include guide structures 452 (such as, for example, wires) that facilitate combining a sampler assembly chamber 460 with the ion-sensor cartridge 400. As illustrated in FIG. 4D, in one embodiment, the sampler assembly includes a tube 461 with one end 463 dimensioned to draw fluid into the chamber 460 and another end 465 abutting the connector portion 420. The tube 461 or other sampler assembly structures, may be combined with the connector portion by any suitable means. For example, the abutting end 465 may be mechanically constrained in place and/or affixed with a suitable epoxy.

Figure 5:
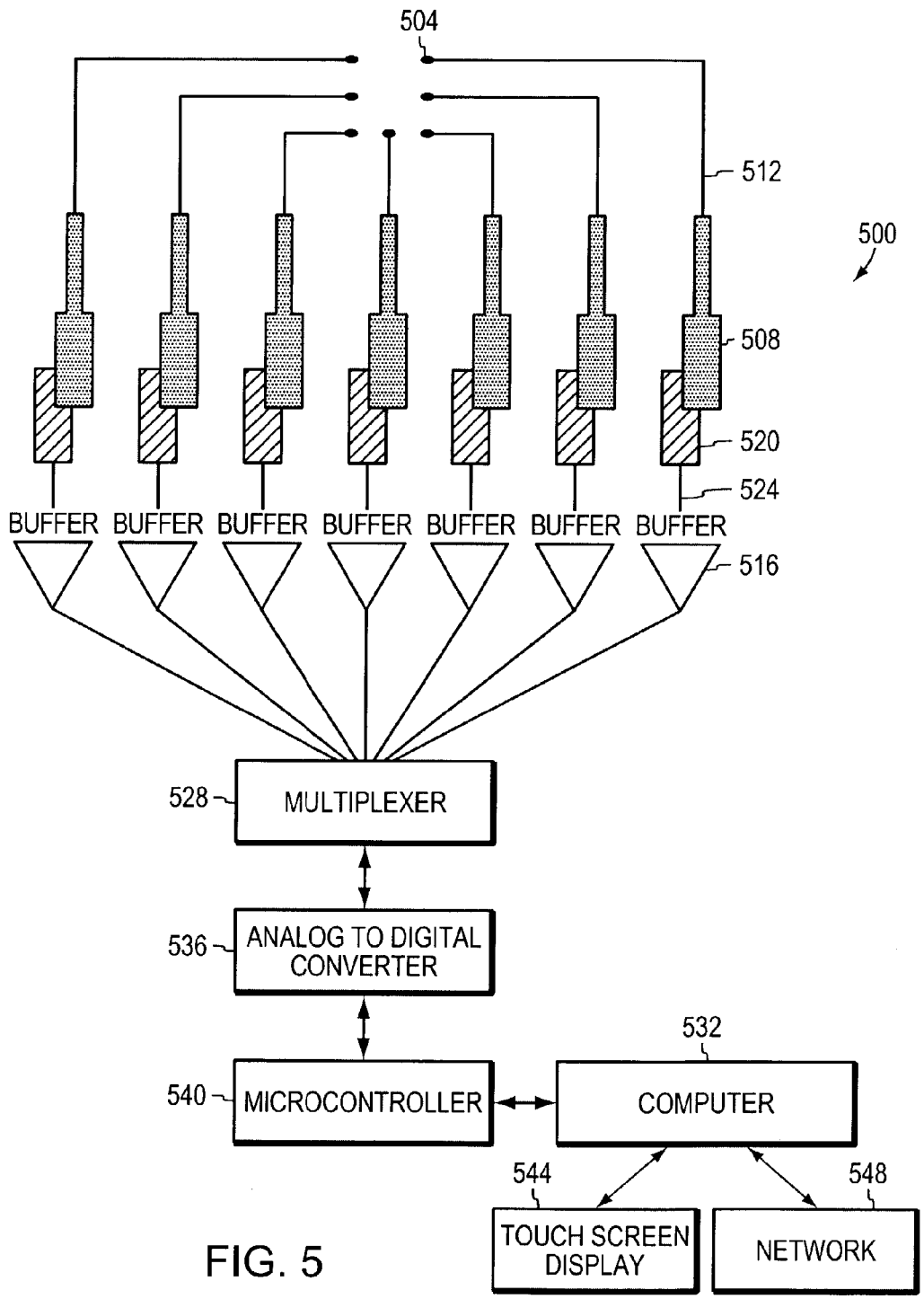
FIG. 5 schematically illustrates one illustrative embodiment of electronics and hardware used to collect and interpret data measured by an ion-selective electrode.

FIG. 5 depicts one illustrative embodiment of electronics and hardware 500 used to collect and interpret the data measured by ion-selective electrodes. Connector pads 504 are connected to interface contacts 508 by interface leads 512. The interface contacts 508 are in electrical communication with corresponding buffers 516. In one embodiment, the buffers 516 are interfaced with the interface contacts using device contacts 502 and device leads 524. The buffers are in electrical communication with a multiplexer 528, which gates electrical signals from the ion-selective electrodes. The multiplexer 528 is in serial electrical communication with a computer 532 via an analog-to-digital converter 536 and a microcontroller 540. The computer 532 calculates electrolyte values using calibration information from the reference electrode, the Nernst equation, and selectivity constants, as described above. The computer 532 may include, for example, a touch screen display 544 to facilitate user interface. The computer 532 may locally access data regarding ranges of expected values or patient history, or the information may be accessed from a network 548.

The following examples are intended to be illustrative, and not limiting.

EXAMPLE #1

Ion-Sensor Cartridge

One embodiment of an ion-sensor cartridge is made according to the following procedure. A plurality of ion-sensor cartridges are produced from a single silicon wafer. Titanium is sputtered to form a layer about 1000 Å thick on the polished surface of a four-inch silicon wafer, and then an approximately 0.2 µm thick layer of semiconductor-quality silver is sputtered onto the surface of the titanium. This titanium layer serves to enhance adhesion of the silver layer. A layer of photoresist is then spun onto the silver layer. The photoresist is soft baked, exposed in a pattern and developed to yield a pattern of photoresist on the silver layer (i.e., a metallization pattern). This metallization pattern includes what will eventually become the ion-selective electrodes, the reference electrodes, lead lines and electrical connector portion of the ion-sensor cartridge. The uncovered silver layer is then chemically etched to expose the titanium layer, and the titanium layer is chemically etched to expose the underlying silicon wafer. The remaining photoresist is then removed, and the resultant coated wafer is cleaned (e.g., "descummed" to remove photoresist and/or carbonaceous films) with an oxygen plasma etch.

Photoresist is again spun on, baked, exposed and developed. This photolithographic step is used to protect all the previously patterned components, except for the ion-selective and reference electrode areas. The exposed ion-selective and reference electrode areas are then exposed to a 0.1 M $FeCl_3$ solution for five minutes to convert the exposed areas to AgCl. The photoresist is then removed with a solvent, such as acetone, and the resultant coated wafer cleaned (e.g., descummed) in an oxygen plasma.

A photosensitive polyimide is then spun on the coated surface of the cleaned wafer and soft baked at approximately 55° C. for 70 minutes to produce a final cured thickness of approximately five microns. Subsequently, a second photolithographic step is used to pattern the polyimide to set out the ion sensitive electrode areas, the reference electrode areas and contact pads of the electrical connection portion of the cartridge. The patterned photoimagable polyimide is then developed and rinsed to remove the imaged polyimide from the metal. The resultant coated wafer is then cleaned again with oxygen plasma. The resultant coated wafer is then put through a cure cycle in a nitrogen-purged oven at approximately 300° C. for 60 minutes to cure the remaining polyimide.

A 5% aqueous solution by weight of glutyraldehyde may be used as an adhesion promoter. The array of sensors on the substrate as described above is immersed in the glutyraldehyde solution for approximately two minutes. The substrate is then dried in a desiccator. The ionophores and reference electrode coatings are then selectively deposited onto the AgCl layer of the appropriate ion-selective or reference electrode area by, for example, selective dispensation using a positive displacement pump. For example, a sodium ionophore, having as an active ingredient a one percent concentration of ETH 2120 in a solution of approximately 25% aliphatic polyurethane, 9% PVC and 66% DOA, is dissolved in THF. The solution is then dispensed onto regions where the sodium ion-selective electrodes are formed.

Similarly, a reference electrode coating is dispensed in solution onto one or more reference electrode areas to form reference electrodes. The coating may be a solution of 0.6% tridodecylmethylammonium chloride, 0.5% potassium tetrakis (para-chlorophenyl) borate in an aromatic polyurethane dissolved in THF. The ionophores and reference electrode coatings are then air dried at 50° C. for one hour. The silicon wafer is then diced to produce a plurality of ion-sensor cartridges having, for example, final dimensions of approximately 0.200 inch by 0.050 inch.

The individual ion-sensor cartridges are then mounted onto a higher level assembly, such as a holder which facilitates handling of the cartridge by, for example, a person wearing gloves or a robot arm. This holder preferably includes electrical contacts for connecting the ion-sensor cartridge to an electronic measuring and/or testing unit, for example, as shown in FIG. 5. Structures that facilitate the alignment and placement of the structures that form the sampler assembly chamber (e.g., a capillary tube) may be employed.

EXAMPLE #2

Miniature Ion-Selective Electrode Sensor

Figure 6:
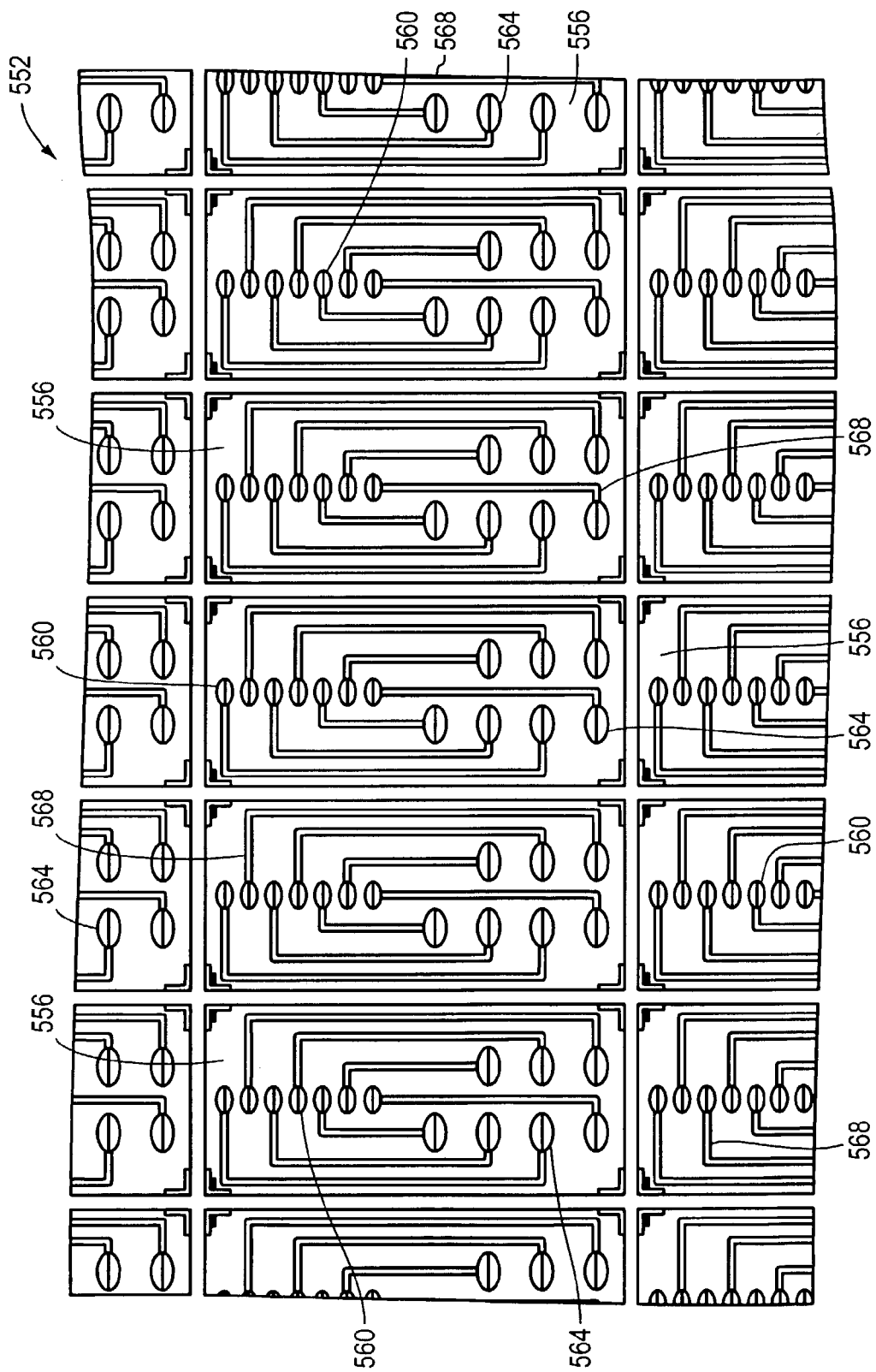
FIG. 6 schematically illustrates a plurality of ion-selective electrode sensors formed on a silicon wafer, according to the invention.

Miniature ion-selective electrode sensors are fabricated on four-inch, silicon wafer substrates. FIG. 6 depicts a portion of a wafer substrate 552 including a plurality of ion-sensor cartridges 556 with seven electrodes. One or more of the seven electrodes are ion-selective electrodes, while the remainder are reference electrodes. Preferably, five of the seven electrodes are ion-selective electrodes, and two are reference electrodes. The wafer substrate 552 is first sputtered with a layer of titanium 1000 Å thick, and is then sputtered with a layer of silver 2000 Å thick. A masking procedure is performed to form the electrode heads 560 and the contact pads 564.

The first mask step protects all of the silver except the areas for the electrode heads 560. The silver is then chloridized to form a 1000 Å thick layer of AgCl on top of 1000 Å of silver. The second mask step protects the areas of the electrode heads 560, contact pads 564, and lead lines 568. The silver and titanium are then etched away from the remaining exposed area. The third mask step uses a photo-imagable polyimide. The polyimide is removed from the electrode heads 560 and the contact pads 564, and serves as an insulator over the remainder of the wafer 552. Ionophores are deposited over the electrode heads 560, and the wafer 552 is then divided into individual ion-selective cartridges 556 each with seven electrodes. The individual sensors 556 may be wire bonded to a larger, easier-to-handle connector, as described above. Preferably, the electrodes have 5 mil diameters, the lead lines are 2 mil wide with at least 2 mil spaces, the contact pads are 10 mil in diameter, and the chip is 50 mil wide and 200 mil long.

Figure 7:
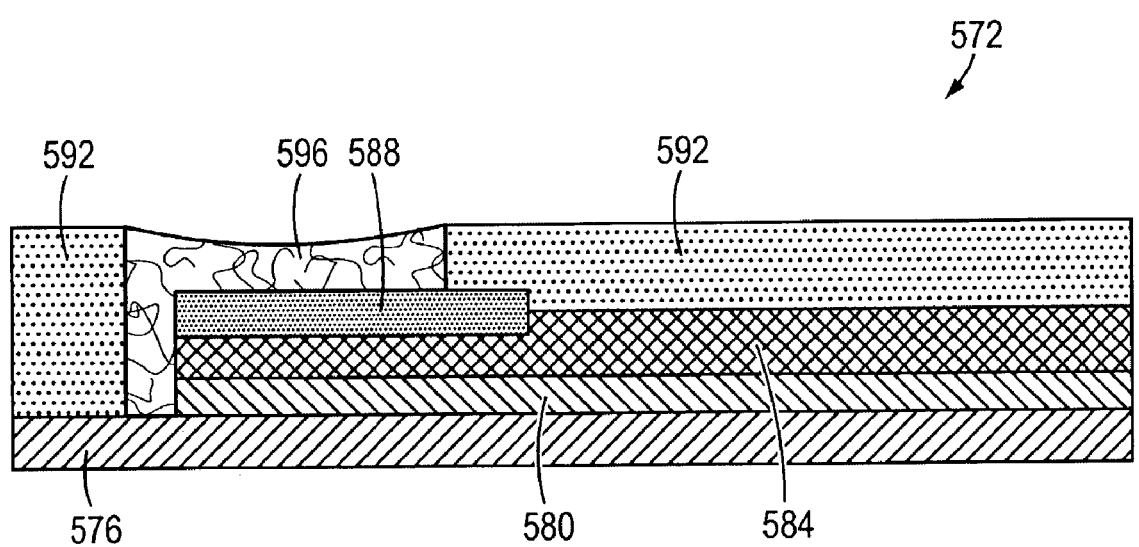
FIG. 7 is a sectional elevation of an ion-selective electrode sensor, according to the invention.

FIG. 7 shows a cross-section of the layers formed on an individual ion-sensor cartride 572. The cartridge 572 includes a substrate 576 on which the titanium layer 580 is sputtered. Preferably, the substrate 576 is silicon. The silver layer 584 is sputtered onto the titanium layer 580. A portion of the silver layer 584 is chloridized to form the AgCl layer 588. Polyimide 592 is then deposited and developed, and then an ionophore 596 is formed.

EXAMPLE #3

Medical Device

Microfluidic ion-selective electrodes, as described in detail above, may be used as part of a medical electrolyte test. In one embodiment, an ion-sensor cartridge is adapted as part of a disposable test without its supporting analyzer system, which may include an electronic controller and a sampler assembly, as described above. The cartridge is well suited for a POC electrolyte test because of its small size and the fact that the interchangeable sensor head is independent from the supporting structures, such as calibration and waste disposal fluid chambers. Moreover, the cartridge does not require blood to be drawn from the patient using a needle or syringe. The cartridge is interfaced with (e.g., plugged in or otherwise attached) the electronic controller, which performs sensor calibration, electrical measurements, data processing, data storage and communication functions.

Figure 8:
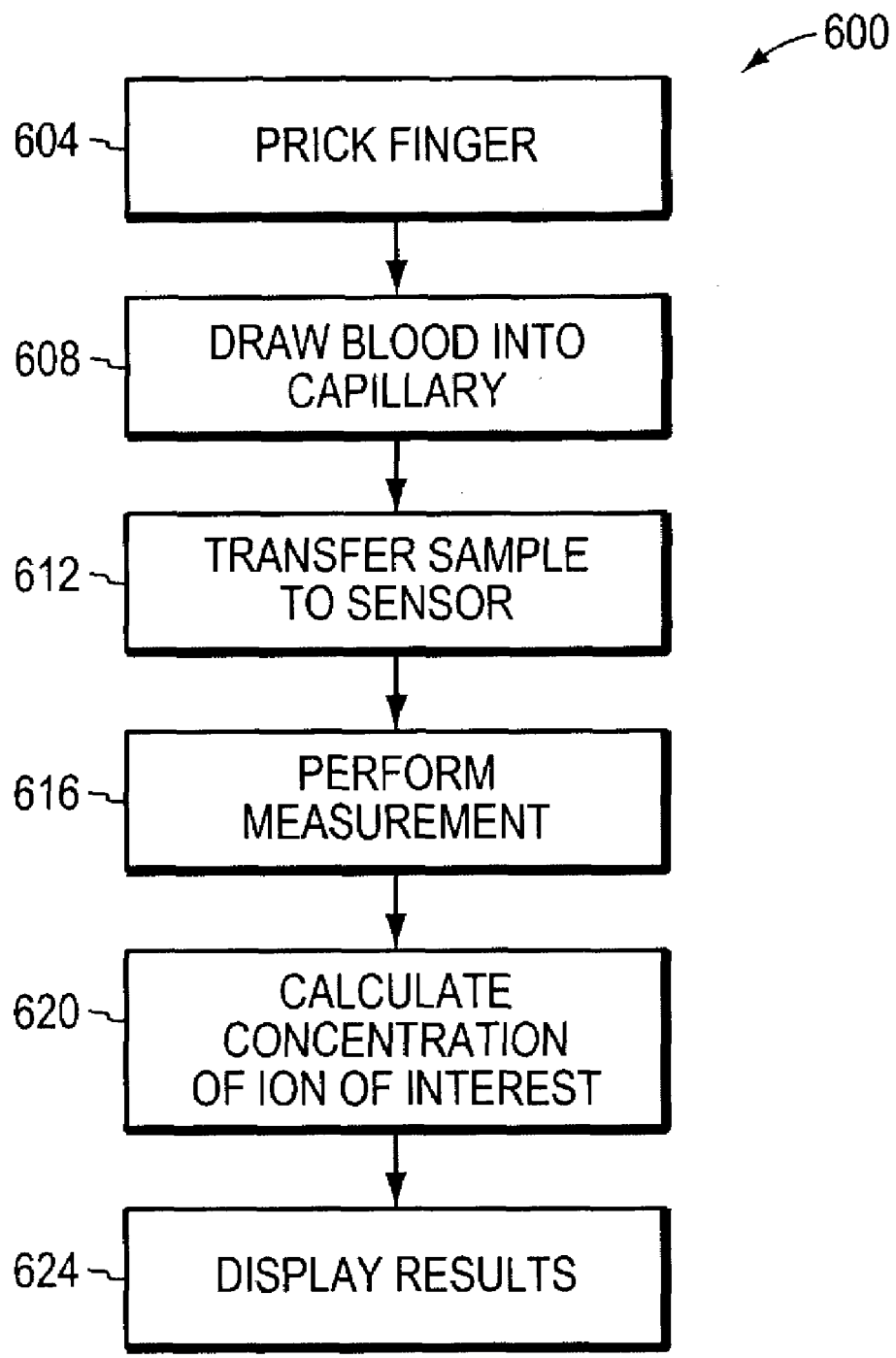
FIG. 8 depicts a flow diagram that illustrates the work flow for performing an electrolyte test using a microfluidic ion-selective electrode.

FIG. 8 depicts a flow diagram 600 that illustrates the work flow for performing an electrolyte test on a subject using miniature ion-selective electrodes formed on the ion-sensor cartridge, according to the invention. A finger of the subject is pricked (step 604) to extract blood. The blood is then transferred to the ion-sensor cartridge. For example, the blood is drawn into a capillary tube (step 608). This requires the equivalent of a single drop or two of blood. The capillary filled with blood is then placed over the cartridge, including an electrode chip, to transfer the blood to the cartridge (step 612).

The electronic controller performs an electrical measurement (step 616) of the electrodes by comparison to one or more reference electrodes. In one embodiment, this measurement is performed after a hydration period. For example, if the ion-sensor cartridge is delivered or stored in a dry state, the hydration period may be, for example, about 30 minutes. The electronic controller has the ability to sense the hydration state of the cartridge by its stability and potentiometric value, so the time period may be adjusted accordingly. During a measurement, the sensor stabilizes approximately 30 to 60 seconds after the application of the blood.

In one embodiment, the ion-sensor cartridge measures a particular electrolyte of interest. Alternately, the cartridge is designed to measure a plurality of electrolytes, as described above. The internal software calculates the concentration(s) of the one or more electrolytes (step 620). Part of the calculation may include calibration offsets and selectivity coefficient corrections. The results of the concentration calculation are then displayed (step 624). Typical displays include a digital report, a numeric display, a print-out from the controller, or a triggering of one or more binary indicators, each indicator corresponding to a concentration range.

While the invention has been particularly shown and described with reference to specific illustrative embodiments, it should be understood that various changes in form and detail may be made without departing from the spirit and scope of the invention as defined by the appended claims.

What is claimed is:

1. An ion-sensor system comprising:
a sampler assembly comprising:
an elongated tube having a proximal end and a distal end and defining a chamber, the proximal end dimensioned to draw a fluid into the chamber by capillary action; and
a connector portion; and an ion-sensor cartridge comprising:
an electrical connection portion interconnecting with the sampler assembly connector portion; and
a plurality of ion-selective electrodes.

2. The ion-sensor system of claim 1, wherein the ion-sensor cartridge further comprises one or more reference electrodes.

3. The ion-sensor system of claim 1, wherein the proximal end comprises a lancet tip.

4. The ion-sensor system of claim 1, wherein the ion-sensor cartridge electrical connection portion is configured as one member of an edge-connector pair.

5. The ion-sensor system of claim 1, wherein the ion-sensor cartridge electrical connection portion is configured as one member of a pin-and-socket connector pair.

6. The ion-sensor system of claim 1, wherein at least one of the plurality of ion-selective electrodes detects at least one of the group consisting of sodium, chlorine, potassium, and calcium in the fluid.

7. The ion-sensor system of claim 1, wherein at least one of the plurality of ion-selective electrodes comprises an electrode layer and an ion-selective layer.

8. The ion-sensor system of claim 7, wherein the electrode layer comprises silver.

9. The ion-sensor system of claim 7, wherein the ion-selective layer comprises an ionophore.

10. The ion-sensor system of claim 9, wherein the ionophore comprises valinomycin.

11. The ion-sensor system of claim 9, wherein the ionophore comprises N,N,N',N'-tetracyclohexyl-1,2-phenylene-dioxydiacetamide.

12. The ion-sensor system of claim 9, further comprising an adhesion promoter anchoring the ionophore to a substrate or a dielectric layer disposed on a substrate.

13. The ion-sensor system of claim 12, wherein the adhesion promoter is glutyraldehyde.

14. A method of fabricating an ion-sensor system, the method comprising the steps of:
providing a substrate;
forming a plurality of ion-selective electrode regions on the substrate;
dividing the substrate into a plurality of strips such that each strip contains a plurality of ion-selective electrodes,
providing a sampler assembly comprising an elongated tube having a proximal end and a distal end and defining a chamber, the proximal end dimensioned to draw a fluid into the chamber by capillary action, and
disposing the strips within the chamber in electrical communication with the sampler assembly.

15. The method of claim 14, further comprising the step of forming one or more reference electrode regions on the substrate.

16. The method of claim 14, further comprising the step of forming an electrical connection portion on the substrate.

17. The method of claim 14, wherein at least one of the plurality of ion-selective electrodes detects at least one of the group consisting of sodium, chlorine, potassium, and calcium in the fluid.

18. The method of claim 14, wherein at least one of the plurality of ion-selective electrodes comprises an electrode layer and an ion-selective layer.

19. The method of claim 18, wherein the electrode layer comprises silver.

20. The method of claim 18, wherein the ion-selective layer comprises an ionophore.

21. The method of claim 14, further comprising applying an adhesion promoter to the substrate or a dielectric layer disposed on the substrate.

22. The method of claim 21, wherein the adhesion promoter is glutyraldehyde.

23. A method of measuring one or more electrolytes in blood, the method comprising the steps of:
extracting blood from a subject;
transferring the blood to an ion-sensor cartridge comprising an ion-selective electrode and disposed within a sampler assembly comprising an elongated tube having a proximal end and a distal end and defining a chamber, the proximal end dimensioned to draw the blood into the chamber by capillary action; and
analyzing one or more electrolytes in the blood.

24. The method of claim 23, wherein the extracting step comprises pricking a finger of the subject.

25. The method of claim 23, wherein the analyzing step comprises interfacing the ion-sensor cartridge with an electronic controller.

* * * * *